(12) United States Patent
Weisel et al.

(10) Patent No.: US 8,066,718 B2
(45) Date of Patent: Nov. 29, 2011

(54) EXPANDABLE NEEDLE SUTURE APPARATUS AND ASSOCIATED HANDLE ASSEMBLY

(75) Inventors: Thomas Weisel, Ventura, CA (US); Martin Padget, Valencia, CA (US)

(73) Assignee: DePuy Mitek, Inc., New Brunswick, NJ (US)

( * ) Notice: Subject to any disclaimer, the term of this patent is extended or adjusted under 35 U.S.C. 154(b) by 0 days.

(21) Appl. No.: 10/803,406

(22) Filed: Mar. 17, 2004

(65) Prior Publication Data
US 2004/0249393 A1 Dec. 9, 2004

Related U.S. Application Data

(60) Provisional application No. 60/455,859, filed on Mar. 18, 2003, provisional application No. 60/500,046, filed on Sep. 3, 2003.

(51) Int. Cl.
*A61B 17/10* (2006.01)

(52) U.S. Cl. .......................................... 606/139; 606/144

(58) Field of Classification Search .................. 606/139, 606/144, 145, 222–227; 132/212, 201
See application file for complete search history.

(56) References Cited

U.S. PATENT DOCUMENTS

| | | | |
|---|---|---|---|
| 3,877,434 A | 4/1975 | Ferguson et al. | |
| 5,281,237 A | 1/1994 | Gimpelson | |
| 5,312,422 A * | 5/1994 | Trott | 606/144 |
| 5,405,354 A | 4/1995 | Sarrett | |
| 5,569,269 A * | 10/1996 | Hart et al. | 606/144 |
| 5,618,290 A * | 4/1997 | Toy et al. | 606/139 |
| 5,741,278 A | 4/1998 | Stevens | |
| 5,817,111 A | 10/1998 | Riza | |
| 6,022,360 A * | 2/2000 | Reimels et al. | 606/144 |
| 6,022,630 A | 2/2000 | Reimels et al. | |
| 6,723,107 B1 * | 4/2004 | Skiba et al. | 606/144 |
| 6,770,084 B1 | 8/2004 | Bain et al. | |
| 6,936,054 B2 * | 8/2005 | Chu | 606/145 |
| 2002/0147456 A1 * | 10/2002 | Diduch et al. | 606/144 |

FOREIGN PATENT DOCUMENTS

| | | |
|---|---|---|
| FR | 2701832 | 1/1993 |
| JP | 01057383 | 3/1989 |
| JP | 62213099 | 3/1989 |
| WO | 9621394 | 1/1996 |
| WO | 0178609 A2 | 4/2001 |
| WO | 0178609 A3 | 4/2001 |

* cited by examiner

*Primary Examiner* — Tuan Nguyen
(74) *Attorney, Agent, or Firm* — Myers Andras Sherman & Zarrabian LLP; Joseph C. Andras

(57) ABSTRACT

A surgical suturing device having an axis extending between a proximal end and a distal end is operable to move a suture through body tissue. A handle assembly is coupled to an elongated shaft having a hollow configuration. An actuating rod is disposed to extend between the handle assembly and the shaft. A needle assembly at the distal end of the actuating rod is movable with the actuating rod between an extended state and a retracted state. Bifurcated portions of the needle assembly define a suture slot, the bifurcated portions have a proximate relationship when the needle assembly is in the retracted state and having a separated relationship when the needle assembly is in the extended state. The needle assembly is biased to the retracted state and the bifurcated portions are biased to the separated relationship.

2 Claims, 12 Drawing Sheets

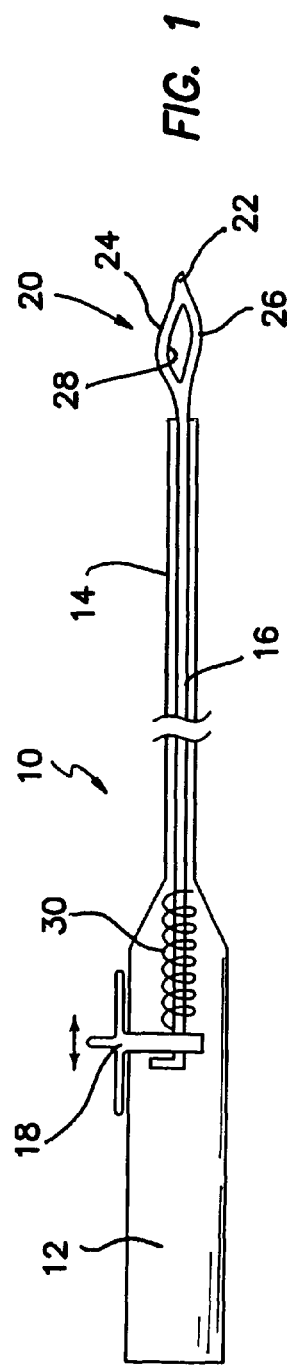
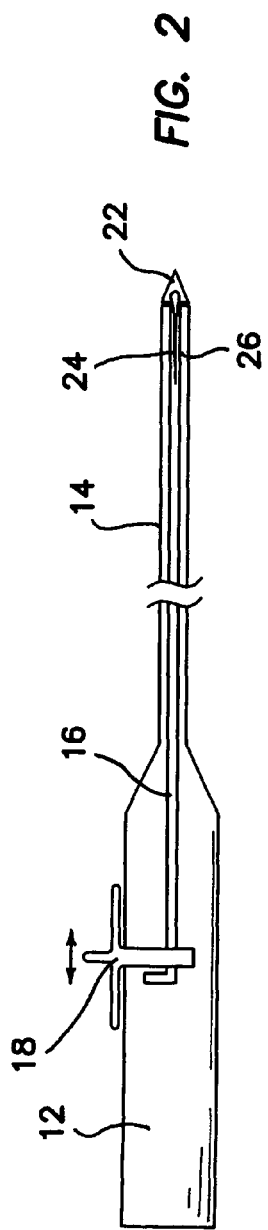
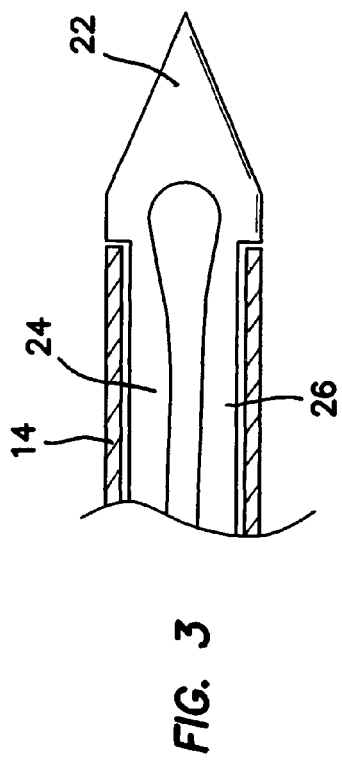

EXPANDABLE NEEDLE SUTURE APPARATUS AND ASSOCIATED HANDLE ASSEMBLY

CROSS REFERENCE TO RELATED APPLICATIONS

This is a non-provisional application claiming the benefit of Provisional Application Ser. No. 60/455,859 filed on Mar. 18, 2003, and entitled, "EXPANDABLE NEEDLE SUTURE APPARATUS AND METHOD," and Provisional Application Ser. No. 60/500,046 filed on Sep. 3, 2003, and entitled, "EXPANDABLE NEEDLE SUTURE APPARATUS AND ASSOCIATED HANDLE ASSEMBLY," both of which are fully incorporated herein by reference.

BACKGROUND OF THE INVENTION

1. Field of the Invention

This invention relates generally to surgical suture apparatus and, more specifically, to needle suture manipulating apparatus and methods.

2. Discussion of Related Art

One of the more challenging aspects of endoscopy/arthroscopy is to properly place a suture in identified tissue. This task is complicated by the fact that all work must be done through a 5-8 millimeter cannula while viewing one's efforts on a monitor.

With these difficult size configurations, it has been a significant challenge to incorporate all of the tasks into a single instrument. As a result, the tasks for initially passing a suture through target tissue and subsequently retrieving the suture from the far side has often required use of more than one instrument.

Various needle configurations have been contemplated, some with the needle permanently attached to the suture and others wherein the needle merely engages the suture. Attempts to miniaturize the needle structure have often produced needles that were so small they tended to yield under compressive stresses.

The handles associated with suturing devices have been limited in the number of functions that could be performed. In some cases, handle assemblies have required two-handed operation. It has also been typical to provide needle assemblies that were permanently attached to the handle rather than assemblies that were removable from the handle and perhaps disposable.

SUMMARY OF THE INVENTION

In one embodiment of the device contemplated, a needle assembly with a sharp tip is shaped from a wire. The wire is partially sliced near the tip so that it has two bifurcated portions that define a slot. The wire is processed in a manner that permits these bifurcated portions to move between two positions. In a first position, the bifurcated portions are biased to extend outwardly in which case the slot is generally open. In the second position, the bifurcated portions can be forced inwardly in which case the slot is substantially closed. As noted, the bifurcated portions are biased outwardly so that the wire, in its relaxed position has an open slot.

In this expanded state, the open slot can be easily loaded with a suture. The needle assembly can then be pulled into a carrier tube that compresses the two bifurcated sides of the slot to shrink the profile of the distal tip and engage the loaded suture. With its sharp tip, the needle assembly, compressed within the outer tube, can then be easily passed with the suture through the tissue. On the other side of the tissue, the needle assembly can be deployed thereby permitting the slot to automatically expand in the relaxed state. This enlarges the slot thereby enabling the suture to be released. The needle assembly can then be removed from the tissue leaving the suture in place.

In one aspect of the invention, a surgical device extends along an axis and has a proximal end and a distal end. The device is operable to move a suture through body tissue and includes a shaft having a hollow configuration. A handle assembly is coupled to the shaft, and an actuating rod having a proximal end and a distal end is disposed to extend between the handle assembly and the shaft. A needle assembly is disposed at the distal end of the actuating rod and is movable with the actuating rod between an extended position and a retracted position. Bifurcated portions of the needle assembly define a suture slot and have a proximate disposition when the actuating rod is in the retracted state and a separated state when the actuating rod is in the extended state. The actuating rod is biased to the retracted position while the bifurcated portions are biased to the separated state.

In another aspect of the invention, a surgical suturing device includes a needle assembly with a needle movable in a needle housing between a free suture state and a captured suture state. A handle assembly includes a longitudinal handle housing sized and configured to releasably receive the needle assembly. A thumb slide assembly is releasably coupled to the needle and movable longitudinally on the handle housing between a distal position and a proximal position. The distal position of the thumb slide assembly is associated with the needle in the free suture state, while the proximal position of the thumb slide assembly is associated with the needle in one of a captured state and a locked state.

In another aspect, the invention includes a method for placing a suture across a body wall of a patient. Initially, a suturing device is provided that includes a hollow shaft with a proximal end and a distal end, an actuating rod disposed in the shaft, and a needle assembly carried by the rod. The arms are movable between a proximate disposition associated with a first slot size and a spaced disposition associated with a second slot size greater than the first slot size. The body wall is then penetrated, with the needle assembly in the retracted position and the arms in the proximate disposition. The needle assembly can then be advanced to the deployed position to move the arms to the spaced disposition associated with the second slot size.

These and other features and advantages of the invention will become more apparent with a description of preferred embodiments in reference to the associated drawings.

DESCRIPTION OF THE DRAWINGS

FIG. 1 is an axial cross section view of one embodiment of the present invention illustrating a bifurcated needle assembly;

FIG. 2 is an axial cross section view showing the needle assembly in a retracted position;

FIG. 3 is an enlarged view of the distal end of the device illustrated in FIG. 2;

FIG. 4 is a side elevation view illustrating the device in a normal state with the needle assembly retracted;

FIG. 5 is a side elevation view showing operation of a thumb slide to deploy the needle assembly to an extended position characterized by automatic formation of an enlarged slot in the needle assembly;

FIG. 6 is a side elevation view illustrating the loading of a suture into the slot of the needle assembly;

FIG. 7 is a side elevation view showing retraction of the needle assembly and capture of the loaded suture;

FIG. 8 is the side elevation view illustrating passage of the needle assembly and suture through tissue;

FIG. 9 is a side elevation view illustrating deployment of the needle assembly to the extended position to enlarge the slot and release the suture prior to withdrawal of the device from the tissue;

FIG. 11 is a side elevation view showing a backing arm and a gathering arm widely separated to receive a suture;

FIG. 12 is a side elevation view illustrating the needle slightly retracted;

FIG. 13 is a side elevation view showing the needle further retracted;

FIG. 14 is a side elevation view showing the needle fully retracted;

FIG. 18 is a side elevation view showing the needle retracted and passed through the tissue;

FIG. 19 is a side elevation view showing the needle fully deployed to receive the suture;

FIG. 20 is a side elevation view showing the needle retracted with the suture disposed in the needle slot;

FIG. 21 is a side elevation view showing the needle removed from the tissue drawing the suture through the needle hole in the tissue;

FIG. 22 is a side elevation view showing the needle fully deployed to release the suture from the needle leaving the suture extending through the tissue;

DESCRIPTION OF PREFERRED EMBODIMENTS

Figure 4:
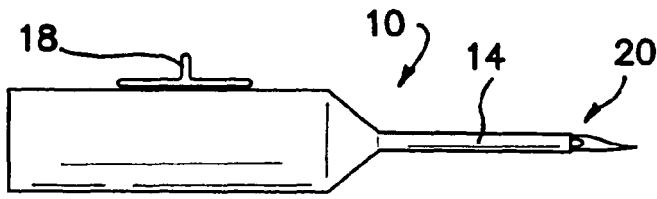
FIG. 4-FIG. 9 illustrate steps in a method for using the suture device of FIG. 1.

A suture device is illustrated in FIG. 1 and designated by the reference numeral 10. The device is an elongate structure and includes a handle 12 at its proximal end and a hollow shaft 14 at its distal end. An actuating rod 16 is disposed within the hollow shaft 14 and extends from the handle 12 through the shaft 14. In the handle 12, the actuating rod 16 is engaged by a thumb slide 18. At its distal end, the actuating rod 16 is coupled to a needle assembly 20. This assembly 20 includes a sharp tip 22 and bifurcated portions 24 and 26, which define a slit or slot 28 proximately of the tip 22.

Operation of the thumb slide 18 relative to the handle 12 moves the actuating rod 16 and the attached needle assembly 20 between an extended position as illustrated in FIG. 1, and a retracted position as illustrated in FIGS. 2 and 3. In this particular embodiment, a spring 30 is used to bias the rod 16 and needle assembly 20 proximally to the retracted position. It will also be noted with reference to FIG. 3 that the needle assembly 20 can be provided with shoulder stops 31 which are separated by a width greater than the internal diameter of the shaft 14. These shoulder stops 31 prevent the distal tip 22 of the needle assembly 20 from entering the shaft 14 in the retracted position.

The bifurcated portions 24 and 26 are also moveable between two positions. In a first position, the bifurcated portions 24 and 26 are separated radially to enlarge the slot 28. In a second position, the bifurcated portions 24 and 26 are brought into close proximately by the tube, closing the slot 28. In a preferred embodiment, these bifurcated portions 24 and 26 are biased to the separated state as illustrated in FIG. 1 so the slot 28 automatically opens when the needle assembly 20 is in the extended position.

Figure 5:
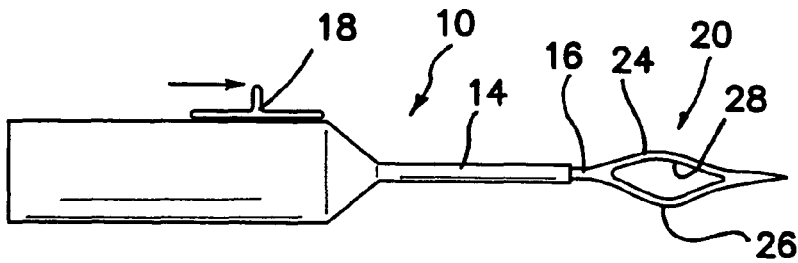
Figure 6:
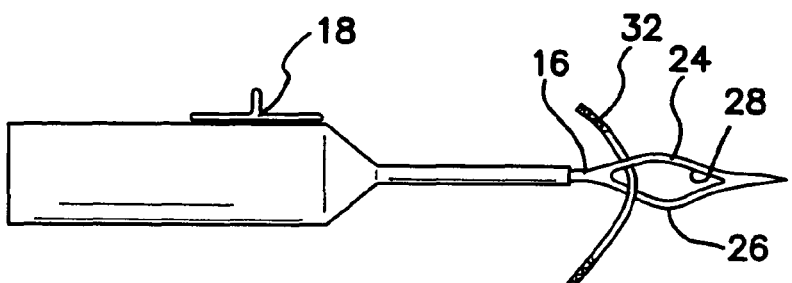
Figure 7:
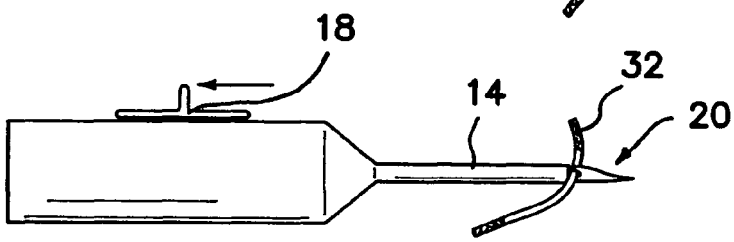
Figure 8:
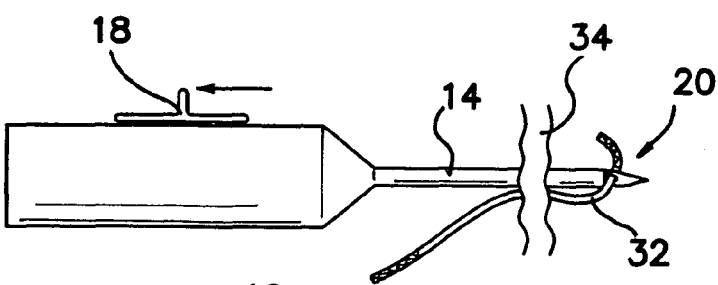

Operation of the suture device 10 is illustrated in FIGS. 4-9. Initially, the device 10 in a relaxed, stored state will have the needle assembly 20 biased to the retracted position as illustrated in FIG. 4. In order to initially load the device 10 with a suture 32, the needle assembly must be moved to the extended position as illustrated in FIG. 5. This is accomplished by pushing the thumb slide 18 distally to force the actuating rod 16 and the needle assembly 20 in the distal direction. When the needle assembly 20 clears the distal end of hollow shaft 14, the bifurcated portions 24 and 26 are free to expand laterally thereby automatically enlarging the slot 28 as illustrated in FIG. 5. With the slot 28 enlarged, the suture 32 can now be passed through the slot as illustrated if FIG. 6. Releasing the thumb slide 18 permits the spring 30 to move the actuating rod 16 and needle assembly 20 proximally to the retracted position. As the needle assembly is drawn into the hollow shaft 14, the restricted radial dimension forces the bifurcated portions 24 and 26 to move toward each other thereby closing the slot 28 and fully engaging the suture 32. In this retracted state, illustrated in FIG. 7, the device is now loaded and prepared for disposition through the patient's tissue, which is designated by the reference numeral 34 in FIG. 8. The actuating rod 16 can be biased to the retracted position so that the device in the relaxed state automatically orients itself for use in crossing the tissue 34 as illustrated in FIG. 8.

Figure 9:
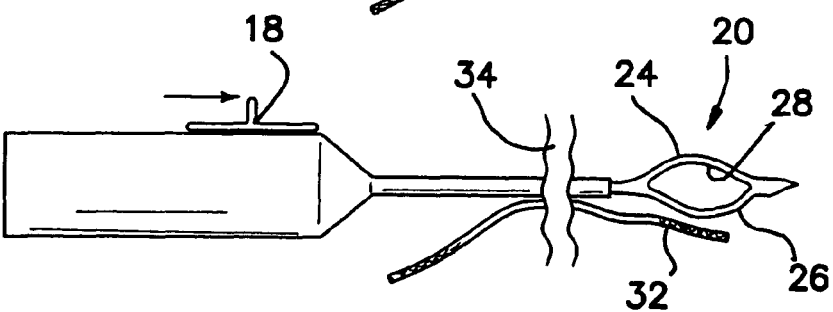

With the needle assembly 20 and the suture 32 extending through the tissue 34, it is now desirable to release the suture from the device 10. This is accomplished by again pushing the thumb slide distally to move the needle assembly from the retracted position to the extended position. As before, the bias of the bifurcated portions 24 and 26 will permit the needle assembly 20 to enlarge the slot 28 thereby facilitating release of the suture 32 from the device 10. This is illustrated in FIG. 9. As a final step, the device 10 can be removed from the tissue 34 leaving the suture 32 operatively disposed across the tissue 34.

Notwithstanding the specific features of this embodiment, it will be noted that the needle assembly 20 includes a sharp point which facilitates passage through the tissue 34 even when the assembly 20 is in the retracted state. The bifurcated portions 24 and 26 function as a gripping means which automatically opens to facilitate loading the suture 32, but which is capable of being closed with a force sufficient to retain the suture in the slot 28 as the device 10 is pushed through the tissue 34. The hollow shaft 14 in this case functions primarily as a vehicle for moving the bifurcated portions 24 and 26 between the open state and the closed state. In the illustrated embodiment the hollow shaft 14 is shown with a straight configuration; but it can also be provided with many different curved configurations to enhance usage in various anatomically restricted areas. It will be apparent to those skilled in the art that this function can be accomplished by many different structures in other embodiments of the concept.

Figure 10:
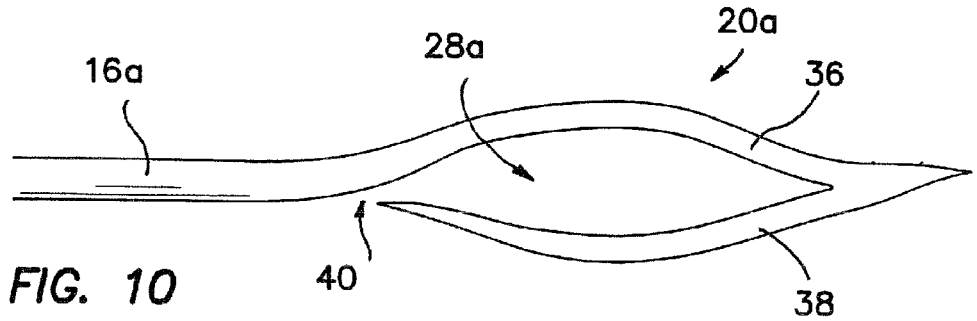
FIG. 10 is a side elevation view showing a further embodiment wherein the needle is fabricated at the proximal end of the slot.

In an additional embodiment illustrated FIG. 10, elements of structure similar to those previously discussed are designated with the same reference numeral followed by the lower case letter "a." Thus, this embodiment includes the actuating rod 16a, needle assembly 20a and distal tip 22a. In this case however, the bifurcated portions 24 and 26 function as a backing arm 36 and gathering arm 38, respectively. The gathering arm 38 can be integral with the backing arm 36 at the distal end of the slot 28a, but preferably is separated from the backing arm 36 at the proximal end of the slot 28a. At this location, the gathering arm 38a is cut from the backing arm 36a to form a passage 40, which allows the needle to be more flexible as it is passed thru curves. The passage 40 can also facilitate drawing the suture into the slot 28a if the passage 40 is exposed distal of the hollow shaft 14a during deployment.

A similar embodiment is illustrated in FIGS. 11-14 wherein elements of structure similar to those previously discussed are designated with the same reference numeral followed by the lower case letter "b." In this embodiment, the hollow shaft 14b receives the actuating rod 16b in the manner previously discussed. This embodiment also includes the backing arm 36b as well as the gathering arm 38b. However, in this case, the gathering arm 38b is integral with the backing arm 36b at the proximal end of the slot 28b. The gathering arm 38b is separated from the backing arm 36b at the distal end where a passage 42 permits the suture to enter the slot 28b. This passage 42 is cut along the gathering arm 38b so that a small portion of the arm 44 remains with the distal tip 22b. This enables the needle assembly 20b to retain the suture without damage when the needle assembly 20b is fully retracted. The gathering arm 38b in this embodiment can be shaped in a variety of ways. In the illustrated example, three bends 46, 48 and 50 create a wide passage 42 to facilitate capture of the suture.

Figure 12:
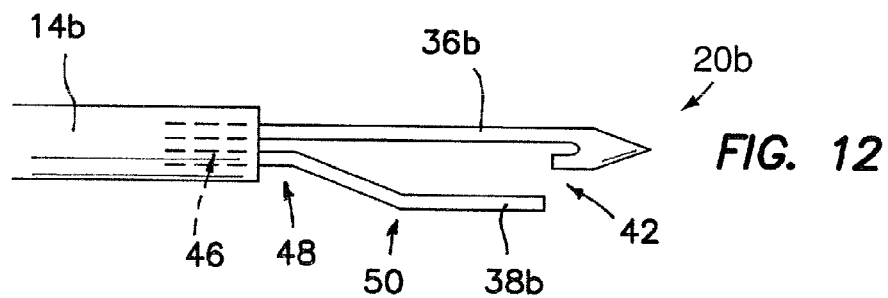

In FIG. 12, the needle assembly 20 has been slightly retracted into the hollow shaft 14b and the bend 46 has been generally straightened. The angle of the bend 50 has created a lip that gathers the suture toward the backing arm 36b as the bend 46 is straightened by the hollow shaft 14b.

Figure 13:
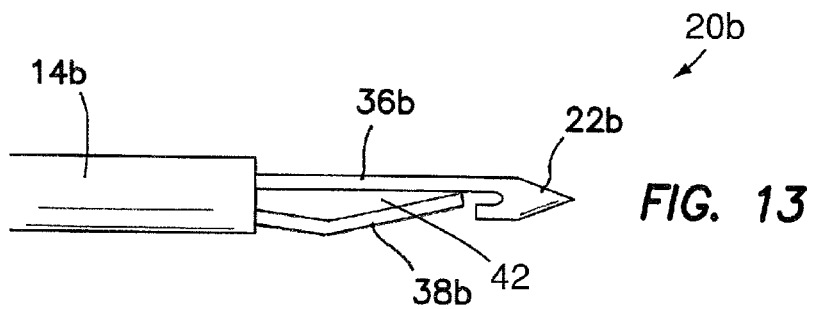

In FIG. 13, the needle assembly 20b is even further retracted. This has caused the bend 48 to straighten bringing the gathering arm 38b into contact with the backing arm 36b while still maintaining the passage 42 for the suture.

Figure 14:
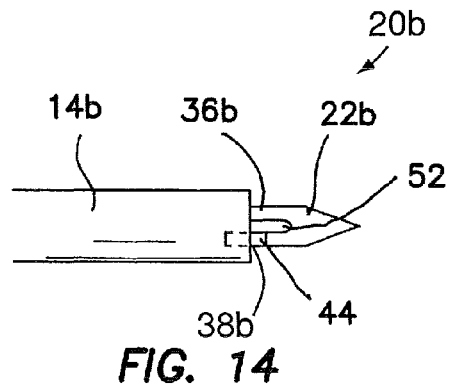

When fully retracted as illustrated in FIG. 14, the short portion 44 of the gathering arm 38b is received in the hollow shaft 14 leaving a small opening 52 to retain the suture.

Figure 15:
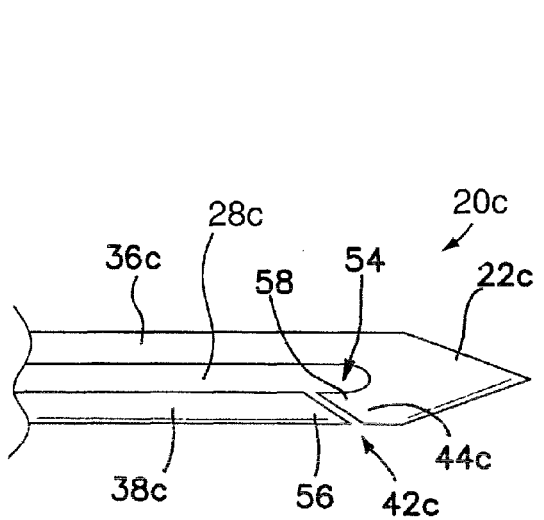
FIG. 15 is a side elevation view of an embodiment similar to FIG. 11, but including a built-in stop.

A further embodiment is illustrated in FIG. 15 where elements of structure similar to those previously discussed are designated with the same reference numeral followed by the lower case letter "c." This embodiment, for example, includes a sharp tip 32c. In this embodiment, the backing arm 36c also defines the slot 28c with the gathering arm 38c. In this embodiment, the gathering arm 38c is also cut to form the passage 42c. However, the cut forming this passage 42c forms an oblique angle with the length of the needle assembly 20c so that a stop 54 is formed at the distal end of the gathering arm 38c. This stop 54 is formed with a proximal tang 56 on the gathering arm 38c, which interferes with a distal tang 58 on the short portion 44c. It is the purpose of this stop 54 to prevent the gathering arm 38c from contacting the backing arm 36c and thereby restricting free movement of a captured suture.

Figure 16:
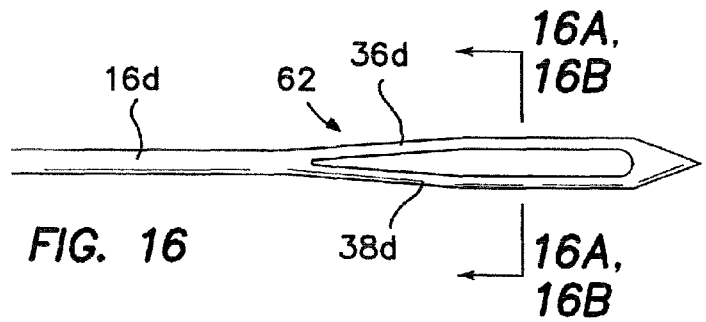
FIG. 16 is a side elevation view of a further embodiment wherein the needle is tapered to facilitate manipulation through drastically bent tubes.
Figure 16A:
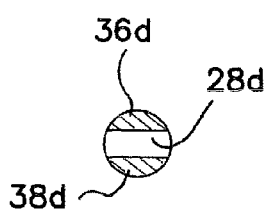
FIG. 16A is a cross section view taken along lines 16A-16A of FIG. 16 showing an embodiment with two arms.
Figure 16B:
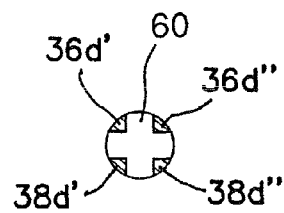
FIG. 16B is a cross section view taken along lines 16B-16B of FIG. 16 showing an embodiment with four arms.

Another embodiment is illustrated in FIGS. 16, 16A and 16B where elements of structure similar to those previously discussed are designated with the same reference numeral followed by the lower case letter "d". In this embodiment, the horizontal slot 28d is formed between the bifurcated portions 24d and 26d. With only the single horizontal slot 28d, this embodiment has a cross-section such as that illustrated in FIG. 16a.

In a similar embodiment, a vertical slot 60 can be added, leaving the needle assembly 20d with four arms which are designated by the reference numerals 36d', 36d", 38d' and 38d" in FIG. 16B. This particular configuration of the needle assembly 20d allows manipulation through drastically bent tubes. Of course, any number of multiple arms could facilitate this advantage. A taper 62 can be formed at the proximal ends of the arms 36d and 38d. This tapered profile keeps the walls of the needle assembly 20d relatively consistent and flexible to minimize stress concentrations.

Figure 17:
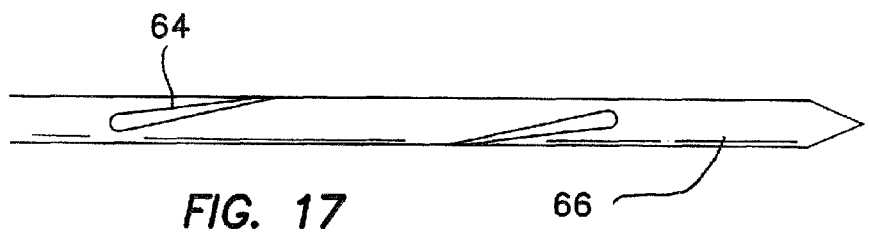
FIG. 17 is a side elevation view of a further embodiment wherein a helical slot is cut around the circumference of the needle.

FIG. 17 illustrates a further embodiment wherein a helical slot 64 is cut around the circumference of a cylindrical needle 66. In this case the helical slot 64 is adapted to receive the suture and to hide the suture within the needle 66 as it penetrates the tissue. In this particular embodiment, the helical slot 64 may have a depth greater than zero but preferably not greater than 0.75 times the radius of the needle 66.

Figure 11:
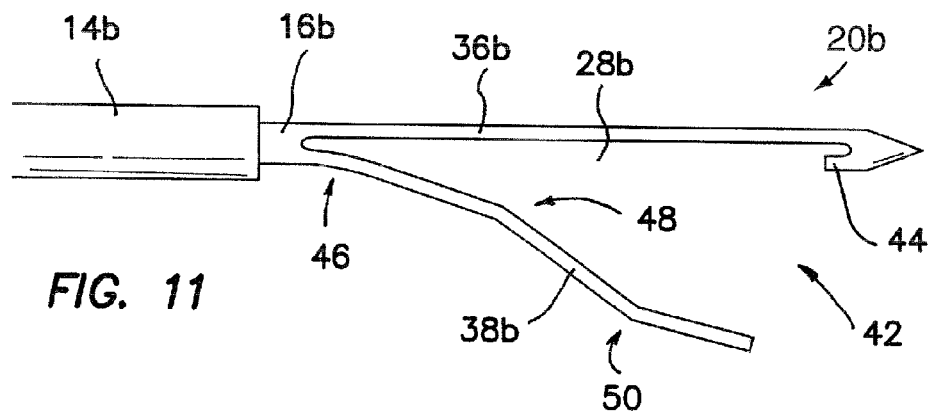
FIGS. 11-14 illustrate a further embodiment wherein the needle is bifurcated at the distal end of the slot.

FIGS. 18-22 illustrate a method for using the needle assembly 20 and particularly the needle assembly 20b illustrated in FIG. 11.

Figure 18:
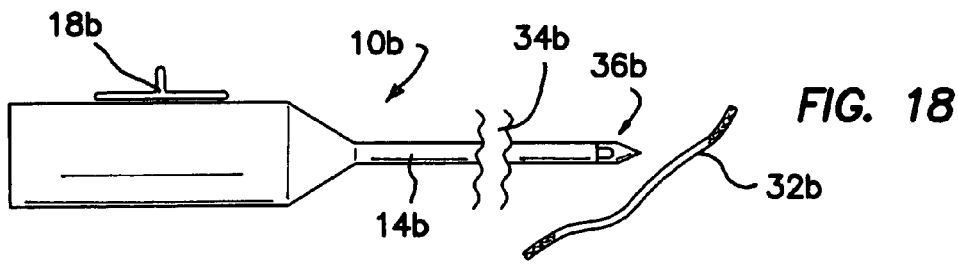
FIGS. 18-22 illustrate a preferred method particularly applicable to the embodiment of FIG. 11.
Figure 19:
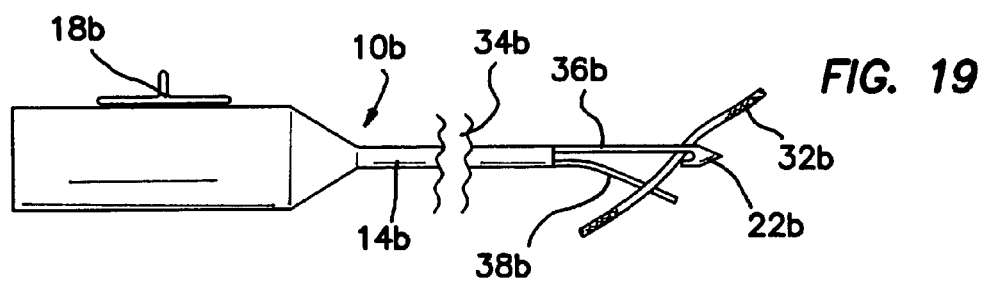

In FIG. 18, the needle assembly 20b has been retracted and the hollow shaft 14b passed through the tissue 34b. The suture 32b is shown on the far side of the tissue 34b. With this disposition of the suturing device 10b, the thumb slide 18b can now be moved distally to deploy the bifurcated needle assembly 20b as illustrated in FIG. 19. In this position, the suture 32b can be introduced through the distal passage 42 and into the slot 28b. As the thumb slide 18b is drawn proximally, the needle assembly 20b is retracted into the hollow shaft 14b in the matter discussed with reference to FIG. 14.

Figure 20:
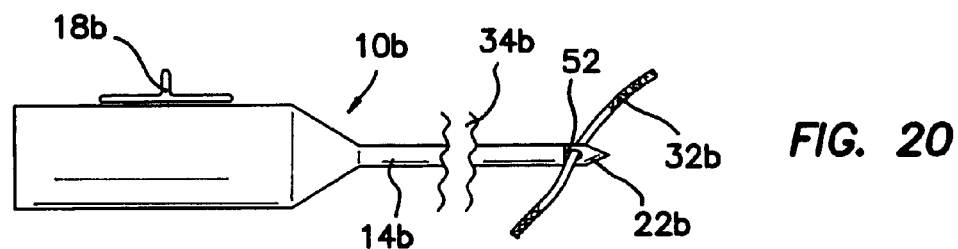
Figure 21:
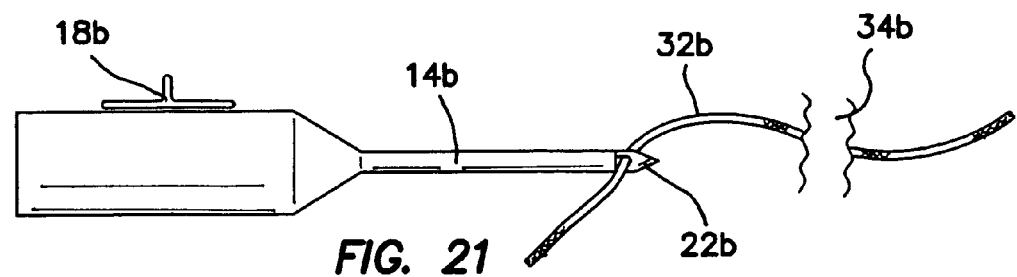
Figure 22:
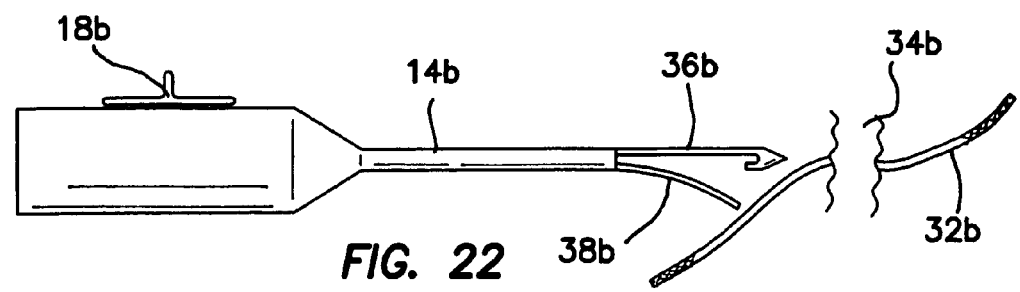

With the suture captured in the opening 52, as illustrated in FIG. 20, the suture device can be withdrawn from the tissue 34b pulling the suture 32b through the needle hole left in the tissue 34b. This step in the process is illustrated in FIG. 21. Finally, the thumb slide 18b can again be moved distally to deploy the needle assembly 20b. This will produce a wide separation of the backing arm 36b and gathering arm 38b resulting in release of the suture 32b from the suture device 10b. In this manner, the suture 32b can be threaded through the tissue 34b.

Figure 23:
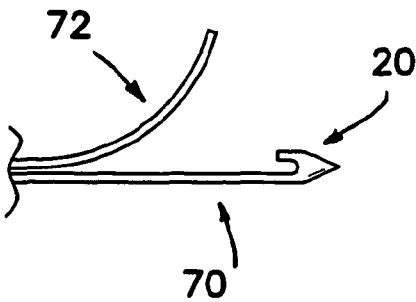
FIG. 23 is a side elevation view of a further embodiment of a needle assembly including a straight backing arm and a curved gathering arm.

A further embodiment of the invention is illustrated in FIG. 23 where the needle assembly 20 is shown with a unique shape that enhances performance in some embodiments. In this case, the needle assembly 20 includes a backing arm 70 and a gathering arm 72. The gathering arm 72 is curved so that an opening is provided with minimal needle deployment to facilitate capture of the suture. This feature enhances use of the needle assembly 20 where the suture must be engaged in small spaces and the needle cannot be fully deployed.

Figure 24:
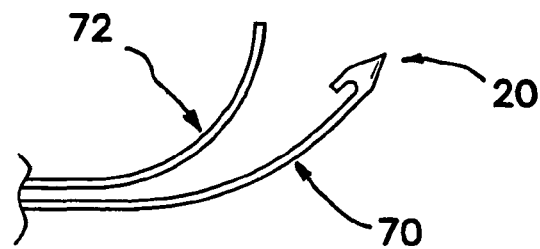
FIG. 24 is a side elevation view of another embodiment including a curved gathering arm and a curved backing arm.

In FIG. 24, a similar embodiment is illustrated where the backing arm 70 is also curved. In this manner, the needle assembly 20 can be provided with a shape that is closer to that of the hollow shaft 14 (FIG. 1). This embodiment is representative of a concept wherein the hollow shaft can have many different curved configurations, each adapted for a particular anatomical area or indication; and the associated needle assembly including the backing arm 70 and gathering arm 72 can be matched to the configuration of the shaft.

Figure 25:
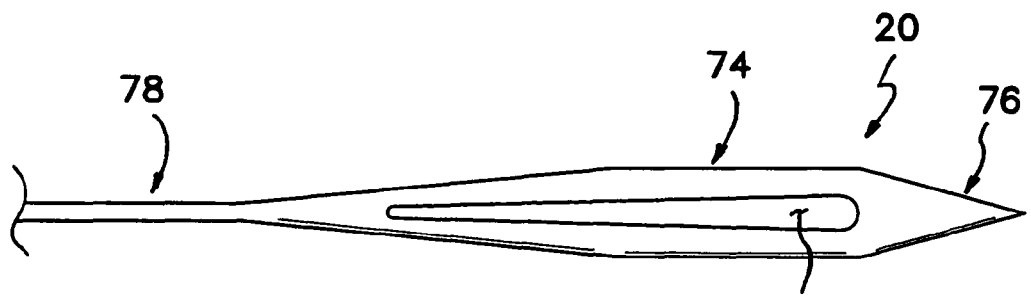
FIG. 25 is another embodiment of a needle assembly with angled portions defining a slot.
Figure 26:
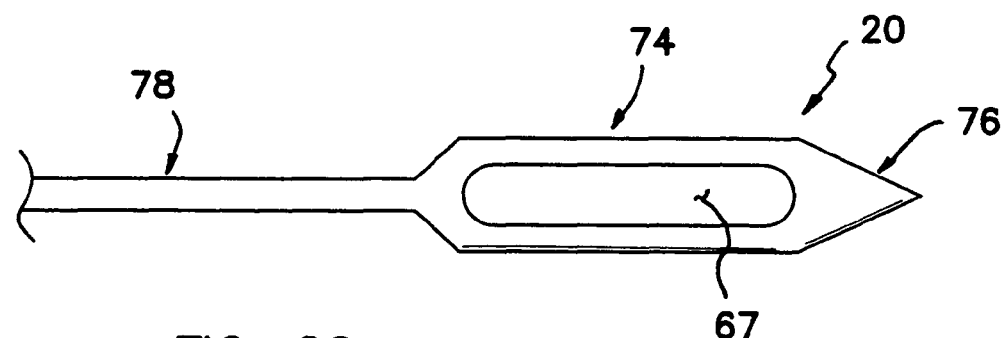
FIG. 26 is a further embodiment of the needle assembly with large and small diameter portions.

FIGS. 25 and 26 show two variations where the needle assembly 20 includes a thick needle section 74 that is proximal of a pointed end 76. In these embodiments, the thick needle section 74 defines a portion of the suture slot 67 that, as previously noted, can have a variety of configurations. Proximal of the thick section 74, a diameter can be made smaller so that a thinner section 78 is created. This thin section 78 makes it easier for the needle to be moved through the curves of the hollow shaft 14.

Figure 27:
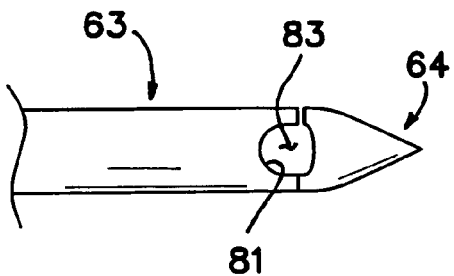
FIG. 27 is a side elevation view of another needle assembly including a notch in the needle tube.

In the embodiment of FIG. 27, a notch 81 is created in the distal end of the hollow tube 63. This notch 81, in connection with a needle tip 64, creates a suture slot 83 which holds the suture. With the notch 81 buried in the hollow tube 63, the needle tip 64 can be made shorter so that a curved device can have a lower profile adapting it for use in a smaller diameter cannula.

Figure 28:
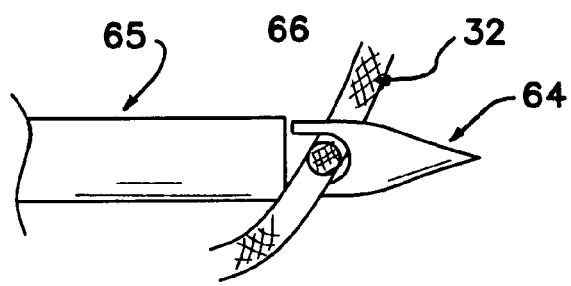
FIG. 28 is a side elevation view illustrating a notch-free needle tube and a needle in a suture-sliding position.
Figure 29:
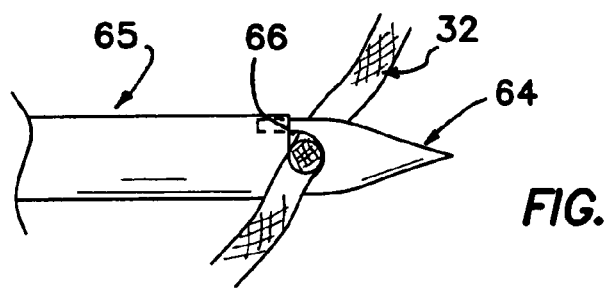
FIG. 29 is a side elevation view similar to FIG. 28 with the needle in a suture-locked position.

FIGS. 28 and 29 illustrate two positions of a needle tip 64 relative to a hollow tube 65. In these two positions, the size of the suture slot 66 can differ. The suture slot 66 in FIG. 28 is sufficiently large to enable the suture to slide or slip easily relative to the hollow tube 65. By comparison, the suture slot 66 in FIG. 29 is relatively small because the needle tip 64 has been retracted slightly into the hollow tube 65. In this second position, the needle tip 64 is retracted to reduce the size of the suture slot 66 and hold or lock the suture in place against the hollow tube 65. A variety of mechanisms can be used to provide various detented positions between the first position illustrated in FIG. 28 and the second position illustrated in FIG. 29. A mechanism could also be provided to require a force of progressive magnitude in order to move between the slipping position of FIG. 28 and the locking position of FIG. 29.

In some cases it is advantageous to provide the hollow shaft 14 with a drastically bent configuration. Under these circumstances, a needle assembly 20 formed from a metal material such a Nitinol, can be made to slide more easily within the drastically bent tube if it is made thinner at those locations where it is to be bent during deployment or retraction. The distal end of the needle assembly 20 can be kept larger so that the diameter of the needle tip is sufficiently thick to withstand any bending stresses. The proximal end need not be made thicker since it functions primarily as a push/pull rod in compression/tension during deployment and retraction.

Figure 30:
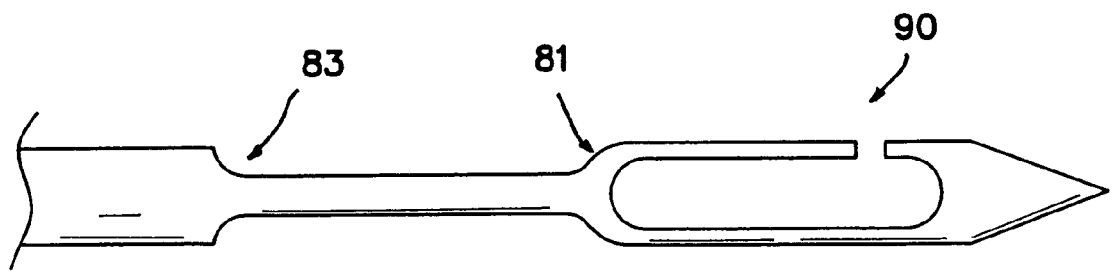
FIG. 30 is a side elevation view of a needle assembly having a bendable section.

FIG. 30 shows an example of a tapered needle that can be provided in a multitude of configurations. Beginning generally at the distal end, the needle 90 can be provided with a distal taper 81. This taper can start at any location between a point just proximal of the needle point to a location just proximal of the slot. In the latter location, the starting position tends to maximize the amount of material defining the slot. Depending on the strength required, a proximal taper 83 can also be provided back to the diameter of the needle point. This proximal taper 83 would be of particular advantage where a thicker shaft might be required for strength purposes.

Figure 31:
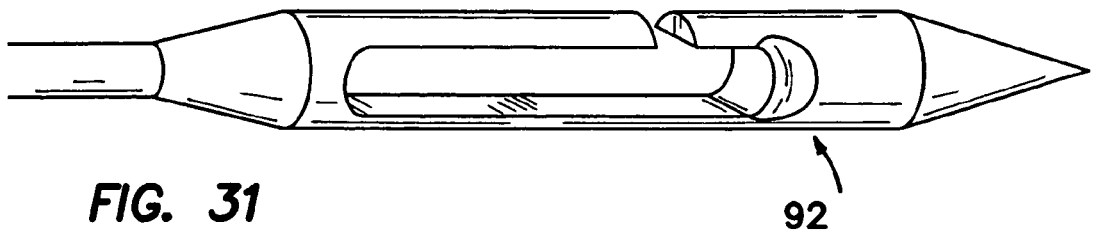
FIG. 31 is a perspective view of the needle assembly having a radius to prevent suture fraying.

As illustrated in FIG. 31, many of the foregoing embodiments can benefit from a radius 92 provided in the distal end of the slot. Such a radius 92 will insure that a sliding suture is less likely to be frayed on a sharp edge.

Figure 32:
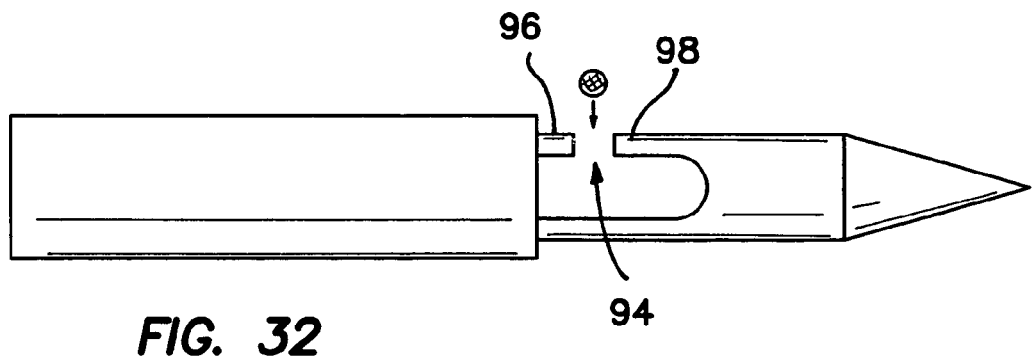
FIG. 32 is a side elevation view of a needle assembly having an opening into the suture slot.
Figure 33:
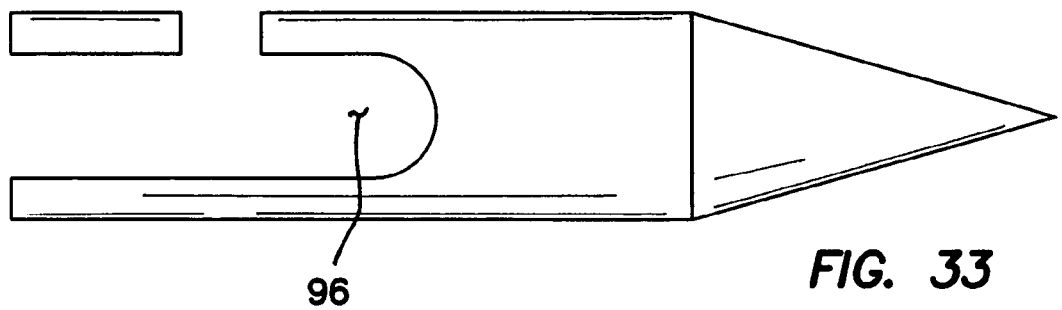
FIG. 33 is a side elevation view illustrating the preferred disposition of the opening.

In the embodiment of FIG. 32, an opening 94 is provided between two tangs 96 and 98, which also define the needle slot. This opening 94 is preferably defined at a location that is more distal along the slot so that it can be exposed when the needle is only slightly deployed from the needle tube. Thus, even with a slight deployment of the needle, a suture can be slid through the opening 94 and into the slot. This can be of particular importance in an embodiment wherein the suture is very close to where the needle exits the tissue. Under these circumstances, it would be more difficult to capture the suture if the needle had to be fully deployed. Notwithstanding the preferred distal location of the opening 94 relative to the slot, it is desirable that the opening 94 be positioned sufficiently proximally that a basin 96 is formed at the proximal end of the slot, as illustrated in FIG. 33.

Figure 34:
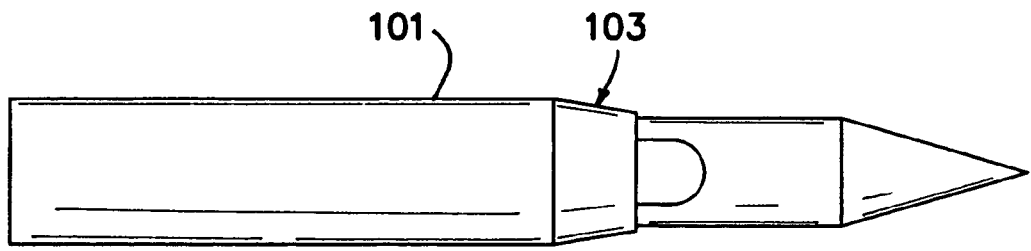
FIG. 34 is a side elevation view illustrating a taper in the needle housing.

FIG. 34 illustrates an embodiment wherein a hollow tube housing 101 is provided with a taper 103 at its distal end. This taper 103 will tend to minimize the insertion forces required for the device.

Figure 35:
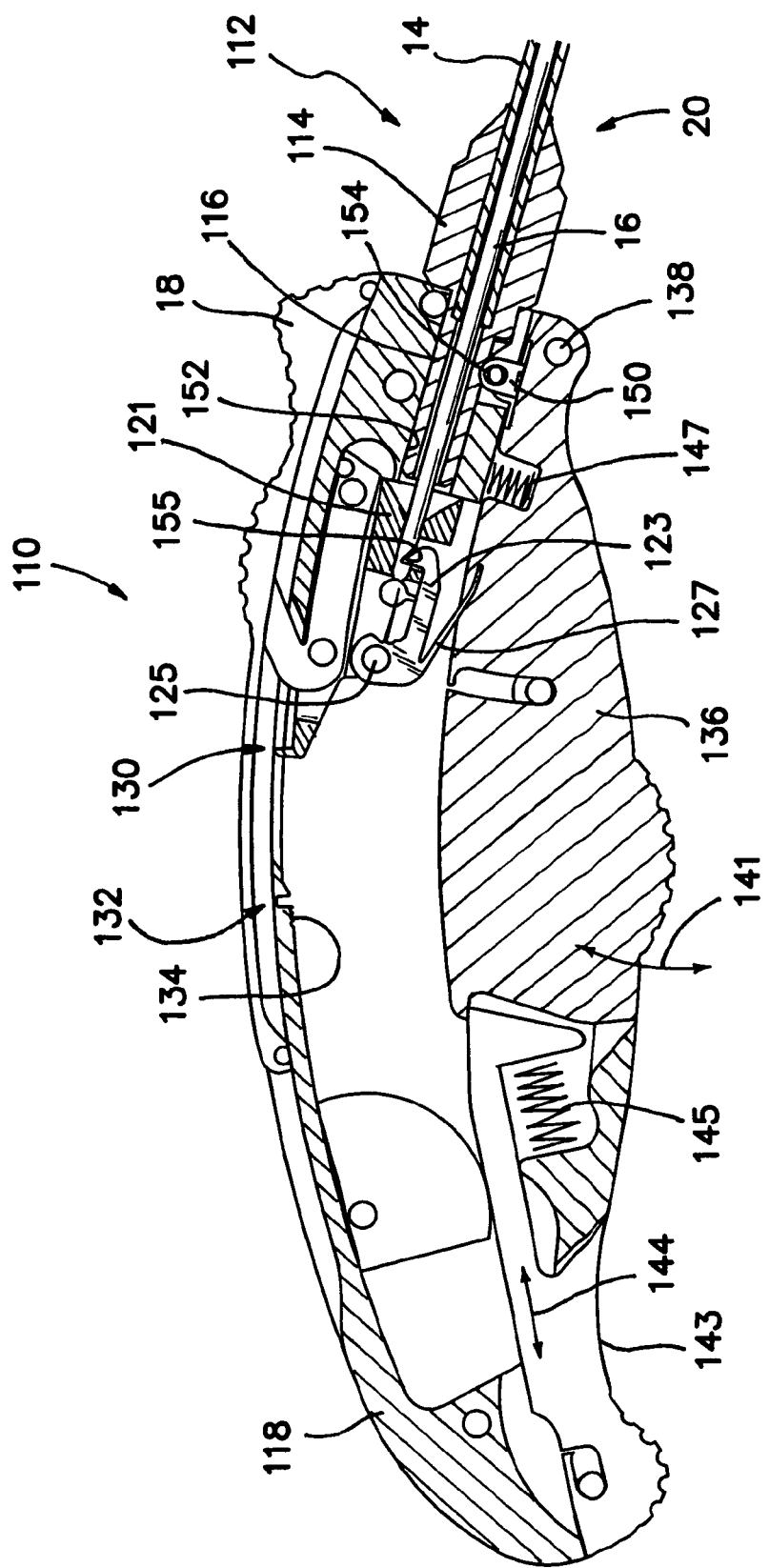
FIG. 35 is a cross-section view of a preferred embodiment of a handle assembly.

A handle assembly 110 is illustrated in FIG. 35 as a preferred embodiment of the handle 12 discussed with reference to FIG. 1. In the manner previously discussed, the handle assembly 110 is adapted to receive the needle assembly 20, including the hollow shaft 14 and the rod 16. In addition, the needle assembly 20 in this embodiment is provided with a hub 112 having an enlargement 74 and a cylindrical extension 116 disposed proximally of the enlargement 74.

In this embodiment, the handle assembly 110 includes a frame 118, and the thumb slide 18 that can be moved by a thumb of the user. In this manner, the thumb slide 18 can be moved between a rearward position, to the left in FIG. 35, and a forward position, illustrated to the right in FIG. 35.

The thumb slide 18 is part of a unit that moves in combination with a slider 121 and a needle latch 123. The needle latch 123 is rotatable on the slider 121 about a pivot pin 125, and includes a leaf spring 127. A tooth 130 is also carried by the slider 121 and cooperates with a slot 132 and ratchet 134 in the frame 118.

A locking lever 136 is pivotal on the frame 118 at a pivot pin 138. This enables the locking lever 136 to move as shown by an arrow 141 between an unlocking position and a locking position illustrated in FIG. 35.

A lever latch 143 is biased by a spring 145 to lock the locking lever 136 in the locking position illustrated in FIG. 35. Movement of the lever latch 143 longitudinally along an arrow 144 and against the bias of the coil spring 145 frees the locking lever 136 to move from the illustrated locking position to the unlocking position under the bias of a coil spring 147.

When the locking lever 136 is in the unlocking position, a hub lock 150 is removed from proximity with the hub 112 of the needle assembly 20. This enables the cylindrical extension 116 of the needle assembly 20 to be inserted into and removed from a channel 152 at the distal end of the handle assembly 110. With the hub 112 inserted into the channel 152, the locking lever 136 can be moved to its locking position where the hub lock 150 engages a slot 154 in the cylindrical extension 116. The lever latch 143 automatically retains the locking lever 136 in the locking position illustrated in FIG. 35.

In order to initially prepare for operation of the suture device 10, the removable needle assembly 20 must be mounted in the handle assembly 110. For purposes of discussion, it will be assumed that the thumb slide 18 is pushed forward into the distal position illustrated in FIG. 35.

As an initial step in the mounting process, the locking lever 136 is moved to the unlocked position, downwardly along the arrow 141 in FIG. 35. This is accomplished by moving the lever latch 143 rearwardly or proximally to the left in FIG. 35. This movement, against the bias of the coil spring 145, will cause the lever latch 143 to disengage the locking lever 136, which will then automatically drop to the unlocking position under the bias of the coil spring 147.

With the hub lock 150 withdrawn from the slot 154, the cylindrical extension 152 of the needle assembly 20 can be moved into the channel 152 along with the needle rod 16. With the needle assembly 20 inserted and the enlargement 114 butted against the handle assembly 110, a notch 155 at the proximal end of the needle rod 16 will engage the needle latch 123. At this point, the locking lever 136 can be closed against the bias of the spring 147 causing the hub lock 150 to engage the slot 154 in the cylindrical extension 152. The closing of the locking lever 136 also provides a positive force through the leaf spring, which maintains the needle latch 123 in the notch 155. As the locking lever 136 moves upwardly to the locking position, the coil spring 145 will bias the lever latch 143 to engage, lock, and retain the locking lever 136 in the locking position. In this operating position, movement of the thumb slide 18 relative to the frame 118 will cause the needle rod 16 to move relative to the hub 114 of the needle assembly 20.

The foregoing procedure for mounting the needle assembly 20 into the handle assembly 110 was begun with the assumption that the thumb slide 18 would be in the forward, distal position. If this is not the case, the needle latch 123 will not initially engage the proximal end of the needle rod 16. Even under these circumstances, the mounting operation can be completed in the foregoing manner so that the hub 114 is retained by the locking lever 136, which is in turn locked by the lever latch 143. With this step completed, the thumb slide 18 can be slid forward in the distal direction to enable the needle latch 123 to engage the notch 155 at the proximal end of the rod 16. This engagement and locking of the rod 16 by the needle latch 123 will be accommodated by deflection of the leaf spring 127. In accordance with either of these processes, the needle assembly 20 can be coupled to the handle assembly 110 and prepared for use by the surgeon.

In operation, the suture 32 can be positioned between the bifurcated portions 24 and 26 of the needle when the needle is deployed. At this point the needle assembly 20 can be fully deployed by moving the thumb slide 10 and the rod 16 distally. In this position of the needle assembly 20, the suture 32 can be loaded, unloaded, picked up, or dropped off as required in different stages of operation.

With the suture 32 thus loaded in the needle assembly 20, the surgeon can pull the thumb slide 18 proximally, rearwardly until the tooth 130 on the slider 121 engages the slot 132 on the frame 118. In this position, the suture 32 is captured within the needle but is still free to slide laterally in the slot of the needle. Note that the springiness of the thumb slide 18 forces the tooth 130 to remain in the slot 132 where it is held in contact with the frame 78.

If it becomes desirable to further engage the suture 32 and eliminate its ability to slide within the needle slot, the thumb slide 18 can be depressed and further retracted causing the tooth 130 to leave the slot 132 and move further rearwardly along the ratchet 134. This slight movement will cause the rod 16 of the needle assembly 20 to move further rearwardly drawing the needle assembly 20 slightly further into the hollow shaft 14. In this position, the suture 32 is not only captured within the needle assembly 20, but is sandwiched and locked between the needle assembly 20 and the hollow shaft 14. During operation of the device 10, the thumb slide 18 in this embodiment is not intended to move further rearwardly.

As it becomes of interest in different stages of operation, the suture 32 can be disengaged by moving the thumb slide 18 from this rearward-most position, forwardly and distally. If the thumb slide is not depressed, the tooth 130 will fall back into the slot 132 where the suture is captured but nevertheless free to slide within the needle eye. In this position, the suture 32 can be removed. By depressing the thumb slide 18 the tooth 130 can be removed from the slot 132 permitting the thumb slide 18 to be moved further in the distal direction. This distal movement will open the bifurcated portions 24 and 26 of the needle assembly 20 and fully releasing the suture 32.

Once the fully operative procedure is completed, the needle assembly 20 can be removed from the handle assembly 110 by reversing the mounting steps previously discussed.

Figure 36A:
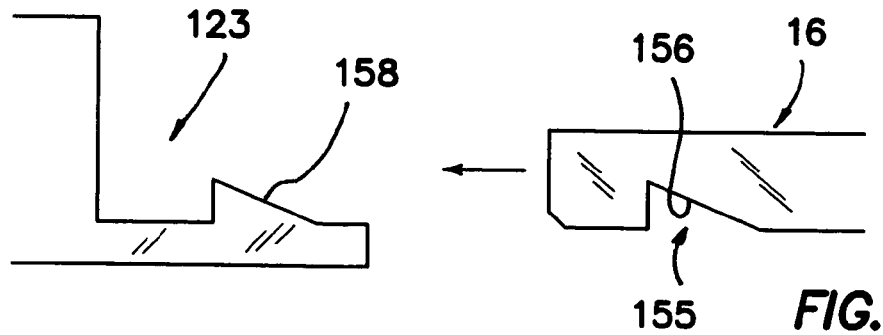
FIGS. 36a-36d are progressive views of a structure and method for coupling the needle assembly and the handle assembly.
Figure 36B:
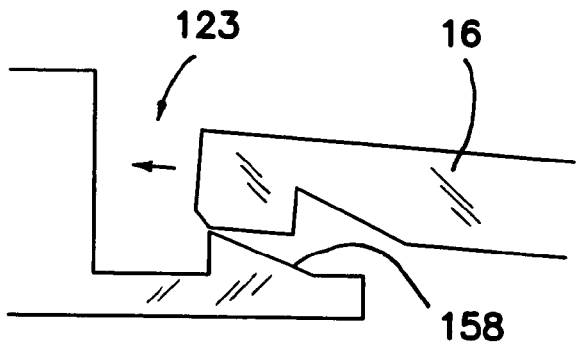
Figure 36C:
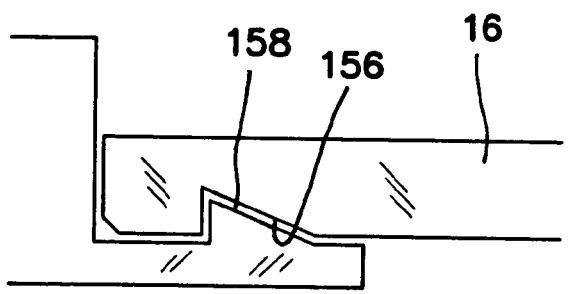
Figure 36D:
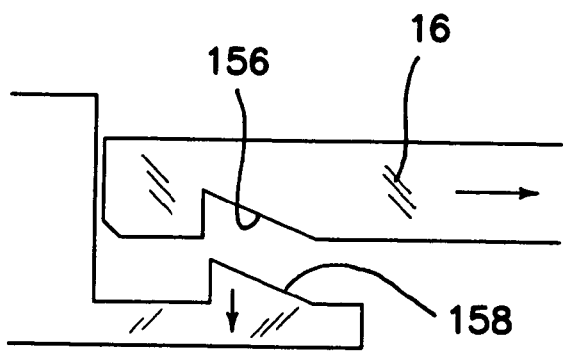

A preferred structure for releasably engaging the needle rod 16 with the needle latch 123 is illustrated in the progressive views of FIGS. 36A-36D. In these views it is shown that the notch 155 can be formed with a ramp 156 that is machined into the proximal end of the needle rod 16. This ramp 156 allows the needle rod 16 to be pushed into the handle assembly 110 when the enlargement 114 of the hub 112 butts against the handle assembly 110, the proximal end of the needle rod 16 can ride up over a ramp 158 on the needle latch 123 as illustrated in FIG. 36B. When fully seated as illustrated FIG. 36C, this locking mechanism keeps the needle assembly attached to the handle assembly until the ramp 158 is moved laterally permitting the ramp 156 and associated needle rod 16 to be moved distally.

Figure 37A:
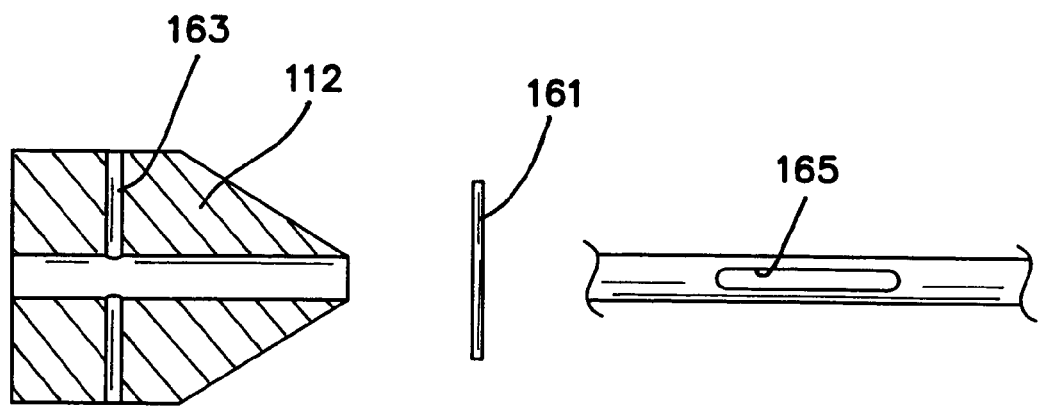
FIGS. 37a and 37b are side elevation views illustrating use of a pin to restrict movement of a needle rod.
Figure 37B:
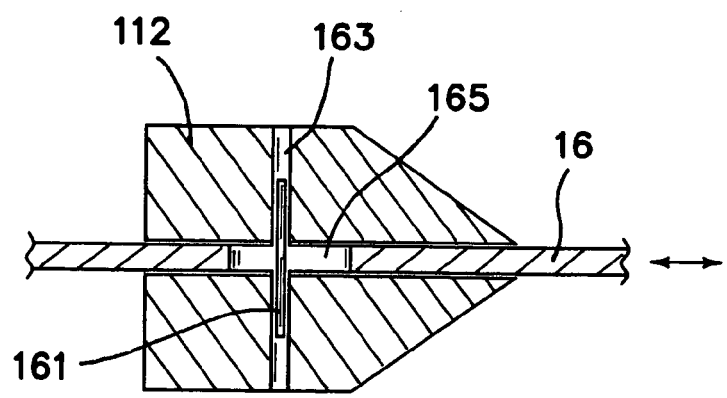

Apparatus for restricting the range of needle movement between its retracted position and its forward position is illustrated in FIGS. 37A and 37B. In this embodiment, a pin 161 is provided for disposition in a transverse slot 163 within the hub 112. In this embodiment, the rod 16 of the needle assembly 20 is also provided with a channel 165 of predetermined length. In this sub-assembly, the rod 16 is initially positioned to extend longitudinally through the hub 112. When the channel 165 intersects the slot 163, the pin 161 can be inserted longitudinally through the slot 163 in the hub 112 and transversely through the channel 165 in the rod 16. This sub-assembly is illustrated in FIG. 37B. The restricted movement provided by this sub-assembly is needed so that the needle is always in a position to be loaded into the handle. With the accommodation of this restricted movement, the needle cannot be jammed in the handle assembly 110.

Figure 38:
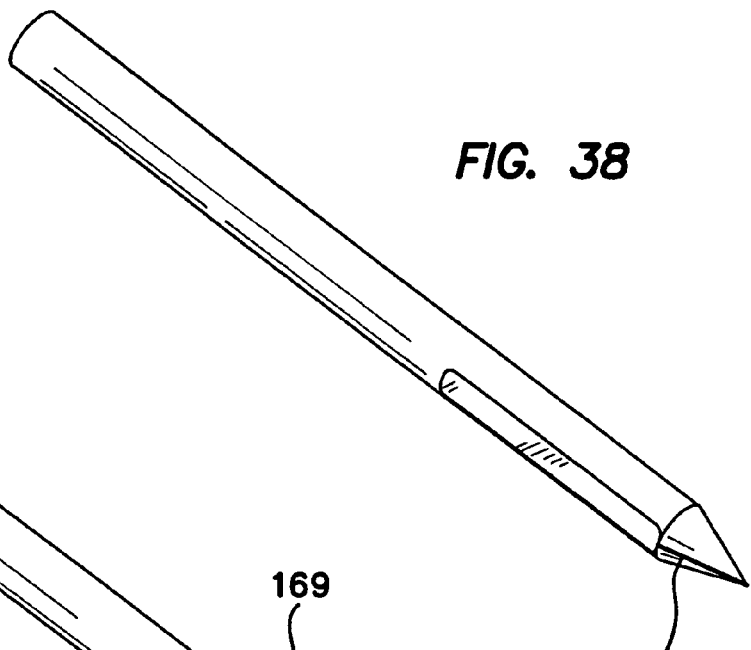
FIG. 38 is a perspective view of a needle assembly bifurcated by a slot.
Figure 39:
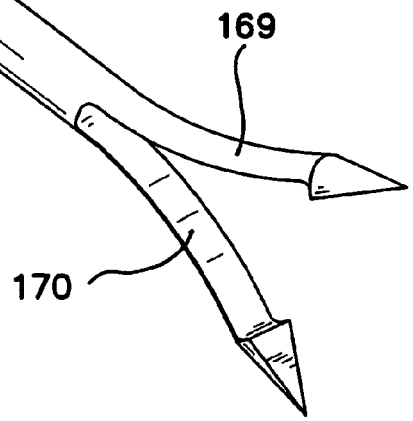
FIG. 39 is a perspective view illustrating the needle of FIG. 38 in its bifurcated configuration.
Figure 41:
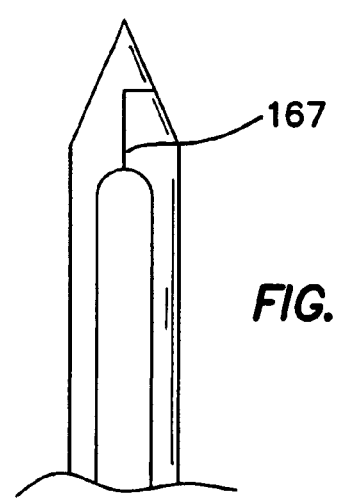
FIG. 41 is a side elevation view of a further embodiment of a bifurcated needle assembly.
Figure 40:
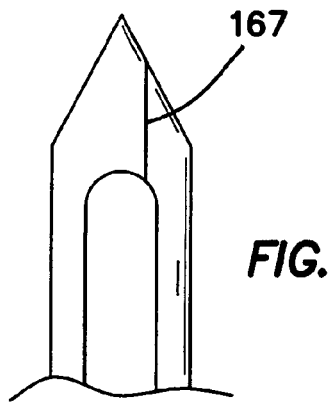
FIG. 40 is a side elevation view of an additional embodiment of a bifurcated needle assembly.

Another unique needle configuration is illustrated the prospective views of FIGS. 38 and 39. In this embodiment, the distal slot is similar to that previously discussed, but the distal tip is bifurcated by a cut 167 that extends into the slot. In operation, deployment of the needle causes the bifurcated portions 169 and 170 to split, as illustrated in FIG. 39. Of course there are many variations of this bifurcated configuration. Two such variations are illustrated in FIGS. 40 and 41. By way of comparison, it will be noted that the cut 167 in FIG. 38 is disposed along the axis of the needle tip so that the tip portions are symmetrical. In the views of FIGS. 40 and 41, the cut 167 does not produce symmetrical tip portions. Although the cut is planar in FIG. 41 and in FIG. 38, it is nevertheless offset from the axis of the tip in FIG. 40. In the embodiment in FIG. 41, the cut 167 is non-planar.

Although the invention has been discussed with reference to specific embodiments, it will be apparent that the concept can be otherwise embodied to achieve the advantages discussed.

The invention claimed is:

1. A surgical device extending along an axis and having a proximal end and a distal end, the device being operable to move a suture through body tissue, comprising:

an elongate shaft having a hollow configuration;

a handle assembly coupled to the shaft;

an actuating rod having a proximal end and a distal end, the actuating rod being disposed to extend between the handle assembly and the shaft;

a needle assembly disposed at the distal end of the actuating rod and movable back and forth with the actuating rod between an extended state relative to the elongate shaft and a retracted state relative to the elongate shaft, the needle assembly being biased to the retracted state;

bifurcated portions of the needle assembly defining a suture slot with a proximal end and a distal end, the bifurcated portions including a backing arm and a gathering arm that are integral with one another at the proximal end of the suture slot, the backing arm and gathering arm having a proximate but spaced relationship when the needle assembly is in the retracted state and having a separated and further spaced relationship when the needle assembly is in the extended state, the backing arm and gathering arm being biased to the separated relationship;

a sharp needle tip formed at a distal end of the backing arm;

a small portion extending proximally from the sharp needle tip to form a hook around an opening at a distal end of the suture slot to retain the suture, a portion of the opening remaining distally of the elongate shaft when the needle assembly is in the retracted state;

a distal end of the gathering arm aligning with the proximally extending portion at a position that is closer to the distal end of the suture slot than the proximal end of the suture slot, and bends in the gathering arm causing the distal end of the gathering arm to extend away from the backing arm to define a wide passage into the suture slot when the needle assembly is in the extended state and the backing arm and gathering arm have the separated relationship, causing the distal end of the gathering arm to extend toward and contact the backing arm while still maintaining a passage for the suture proximal of where the distal end of the gathering arm contacts the backing arm in order to gather the suture with the passage when the needle assembly is in a partially retracted position, and causing the distal end of the gathering arm to substantially align with the small portion extending from the sharp needle tip when the needle assembly is in the retracted state.

2. The surgical device recited in claim 1 wherein the bifurcated portions of the needle assembly have an outer surface in the shape of a cylinder.

\* \* \* \* \*